United States Patent
Ishibashi et al.

(10) Patent No.: US 10,420,455 B2
(45) Date of Patent: Sep. 24, 2019

(54) IMAGING MODULE AND IMAGING SYSTEM INCLUDING SAME

(71) Applicant: FUJIKURA LTD., Tokyo (JP)

(72) Inventors: Kenichi Ishibashi, Sakura (JP); Kenichi Nakatate, Sakura (JP)

(73) Assignee: FUJIKURA LTD., Tokyo (JP)

( * ) Notice: Subject to any disclaimer, the term of this patent is extended or adjusted under 35 U.S.C. 154(b) by 796 days.

(21) Appl. No.: 14/700,234

(22) Filed: Apr. 30, 2015

(65) Prior Publication Data

US 2015/0320297 A1 Nov. 12, 2015

(30) Foreign Application Priority Data

May 8, 2014 (JP) ................................ 2014-097054

(51) Int. Cl.
| | | |
|---|---|---|
| *A61B 1/00* | (2006.01) | |
| *A61B 1/05* | (2006.01) | |
| *H04N 5/225* | (2006.01) | |
| *A61B 90/00* | (2016.01) | |

(52) U.S. Cl.
CPC ...... *A61B 1/00142* (2013.01); *A61B 1/00006* (2013.01); *A61B 1/00045* (2013.01); *A61B 1/00055* (2013.01); *A61B 1/00062* (2013.01); *A61B 1/00103* (2013.01); *A61B 1/00105* (2013.01); *A61B 1/00128* (2013.01); *A61B 1/05* (2013.01); *A61B 1/053* (2013.01); *A61B 1/0002* (2013.01); *A61B 2090/0803* (2016.02); *H04N 2005/2255* (2013.01)

(58) Field of Classification Search
CPC ........ A61B 1/00062; A61B 2090/0803; A61B 1/00142; A61B 1/00006; A61B 1/00045; A61B 1/00103; A61B 1/00105; A61B 1/00128

USPC .................................................. 600/103, 117
See application file for complete search history.

(56) References Cited

U.S. PATENT DOCUMENTS

| | | | | |
|---|---|---|---|---|
| 4,862,872 A | * | 9/1989 | Yabe .................. | A61B 1/00057 600/133 |
| 4,979,497 A | * | 12/1990 | Matsuura ........... | A61B 1/00068 348/65 |
| 4,996,975 A | * | 3/1991 | Nakamura ......... | A61B 1/00055 348/74 |

(Continued)

FOREIGN PATENT DOCUMENTS

| | | |
|---|---|---|
| JP | 3-4831 A | 1/1991 |
| JP | 7-171090 A | 7/1995 |

(Continued)

OTHER PUBLICATIONS

European Search Report dated Sep. 16, 2015 issued in counterpart EP Application No. 15166298.8, (7 pages).

(Continued)

*Primary Examiner* — Timothy J Neal
*Assistant Examiner* — Jae Woo
(74) *Attorney, Agent, or Firm* — Westerman, Hattori, Daniels & Adrian, LLP

(57) ABSTRACT

An imaging module is capable of being used a two or more limited number of times. The imaging module includes: a CMOS imaging sensor; and a counter memory in which the number of use times is stored, the number of use times being the number of times the imaging sensor is used.

8 Claims, 4 Drawing Sheets

(56) References Cited

U.S. PATENT DOCUMENTS

| | | | | |
|---|---|---|---|---|
| 5,068,719 A * | 11/1991 | Tsuji | ............... | A61B 1/042 |
| | | | | 348/65 |
| 5,313,935 A * | 5/1994 | Kortenbach | ....... | A61B 1/00062 |
| | | | | 116/221 |
| 5,469,841 A * | 11/1995 | Kobayashi | ......... | A61B 1/00124 |
| | | | | 600/158 |
| 5,697,885 A * | 12/1997 | Konomura | ........... | H04N 1/2175 |
| | | | | 348/65 |
| 5,830,121 A * | 11/1998 | Enomoto | ........... | A61B 1/00059 |
| | | | | 600/117 |
| 5,896,166 A | 4/1999 | D'Alfonso et al. | | |
| 5,967,969 A | 10/1999 | Enomoto et al. | | |
| 6,078,353 A * | 6/2000 | Yamanaka | .............. | A61B 1/045 |
| | | | | 348/65 |
| 6,298,255 B1 * | 10/2001 | Cordero | ............. | A61B 5/04085 |
| | | | | 600/372 |
| 6,413,210 B1 * | 7/2002 | Enomoto | ........... | A61B 1/00055 |
| | | | | 362/574 |
| 7,001,330 B2 * | 2/2006 | Kobayashi | ......... | A61B 1/00059 |
| | | | | 600/117 |
| 8,310,530 B2 * | 11/2012 | Bayer | ................. | A61B 1/0005 |
| | | | | 348/65 |
| 2003/0174205 A1 * | 9/2003 | Amling | .............. | A61B 1/00059 |
| | | | | 348/65 |
| 2004/0024290 A1 * | 2/2004 | Root | .................. | A61B 1/00016 |
| | | | | 600/160 |
| 2004/0087832 A1 * | 5/2004 | Glukhovsky | ...... | A61B 1/00062 |
| | | | | 600/118 |
| 2005/0129108 A1 * | 6/2005 | Bendall | ............. | A61B 1/00039 |
| | | | | 375/240.01 |
| 2007/0030345 A1 * | 2/2007 | Amling | .............. | A61B 1/00016 |
| | | | | 348/73 |
| 2007/0049798 A1 * | 3/2007 | Urasaki | ............. | A61B 1/00011 |
| | | | | 600/118 |
| 2007/0252798 A1 * | 11/2007 | Wu | ...................... | G09G 3/3614 |
| | | | | 345/87 |
| 2008/0108870 A1 * | 5/2008 | Wiita | ..................... | A61B 1/05 |
| | | | | 600/112 |
| 2009/0030295 A1 * | 1/2009 | Shioi | .................... | A61B 1/227 |
| | | | | 600/316 |
| 2009/0227839 A1 * | 9/2009 | Shimada | ............ | A61B 1/00055 |
| | | | | 600/118 |
| 2010/0141744 A1 * | 6/2010 | Amling | .............. | A61B 1/00016 |
| | | | | 348/68 |
| 2010/0238278 A1 * | 9/2010 | Rovegno | ............ | A61B 1/00052 |
| | | | | 348/75 |
| 2011/0037876 A1 * | 2/2011 | Talbert | ............... | A61B 1/00055 |
| | | | | 348/231.99 |
| 2011/0193948 A1 * | 8/2011 | Amling | .............. | A61B 1/00006 |
| | | | | 348/68 |
| 2011/0218457 A1 | 9/2011 | Song et al. | | |
| 2013/0300847 A1 * | 11/2013 | Hashimoto | ........ | A61B 1/00006 |
| | | | | 348/65 |
| 2014/0182350 A1 * | 7/2014 | Bhavaraju | ........... | G01M 99/008 |
| | | | | 73/1.02 |
| 2015/0305603 A1 * | 10/2015 | Gal | .................... | A61B 1/00167 |
| | | | | 600/103 |
| 2017/0085825 A1 * | 3/2017 | Okawa | ..................... | A61B 1/04 |

FOREIGN PATENT DOCUMENTS

| | | |
|---|---|---|
| JP | 2005237419 A | 9/2005 |
| JP | 2009-148420 A | 7/2009 |
| JP | 2010-88720 A | 4/2010 |

OTHER PUBLICATIONS

Office Action dated Aug. 22, 2017, issued in counterpart Japanese Application No. 2014-097054, with English machine translation. (9 pages).

Office Action dated Nov. 7, 2017, issued in counterpart Japanese Application No. 2014-097054, with English translation. (5 pages).

* cited by examiner

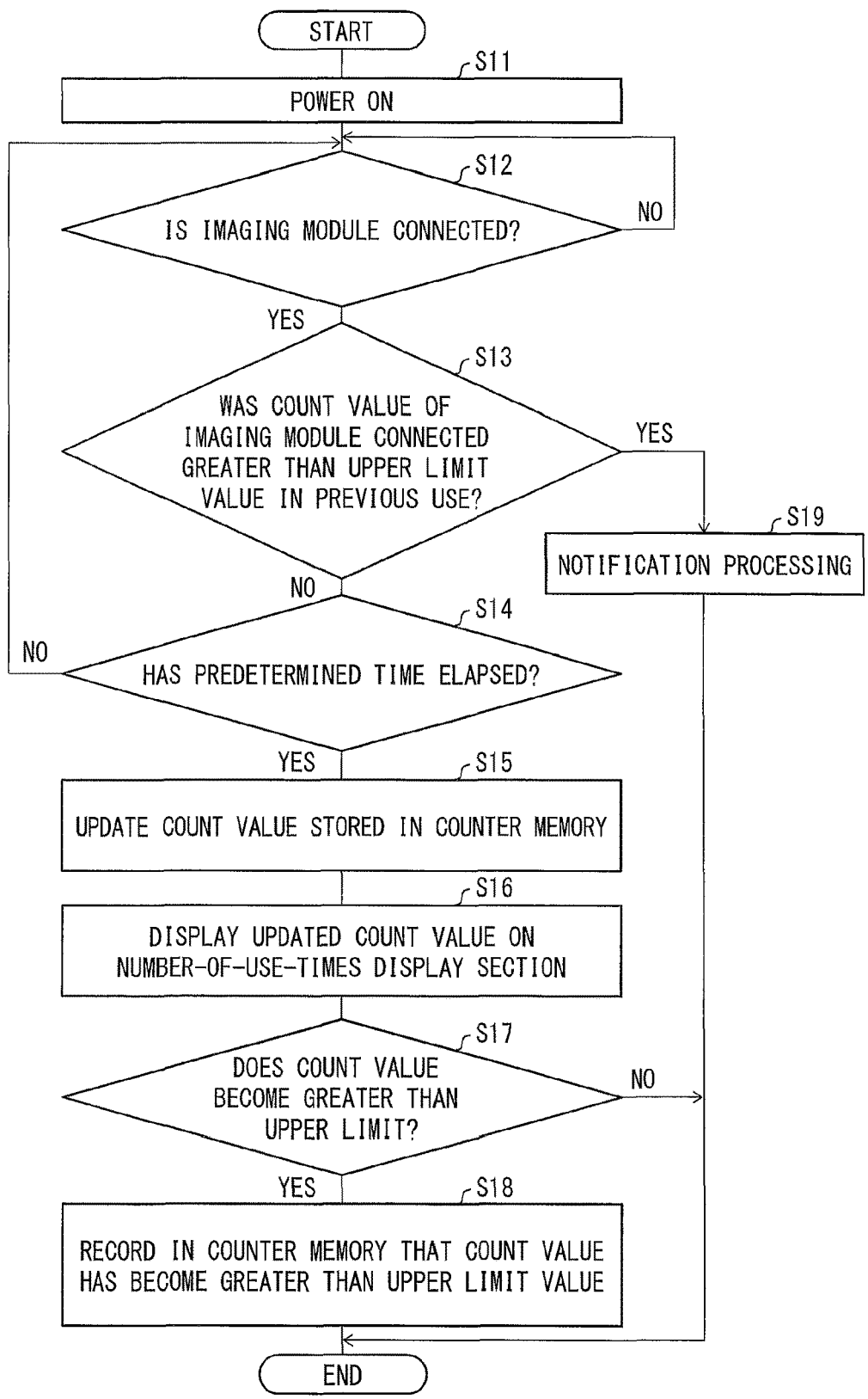

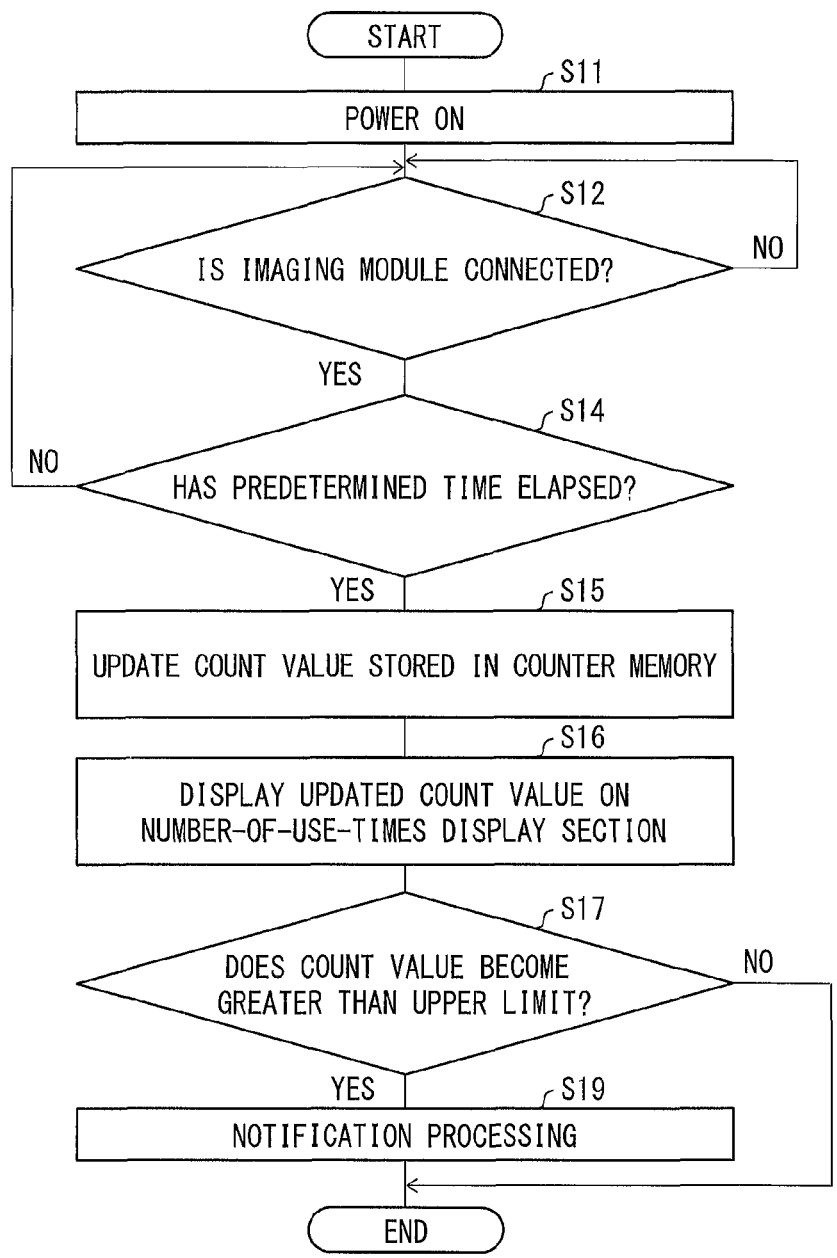

IMAGING MODULE AND IMAGING SYSTEM INCLUDING SAME

This Nonprovisional application claims priority under 35 U.S.C. § 119 on Patent Application No. 2014-097054 filed in Japan on May 8, 2014, the entire contents of which are hereby incorporated by reference.

TECHNICAL FIELD

The present invention relates to an imaging module capturing, for example, an image inside a human body, and an imaging system including the same.

BACKGROUND ART

Conventionally, an imaging system such as an endoscope system has been heavily used in a medical field or in a field of inspecting various machines and facilities. Such an imaging system (i) captures images inside living bodies such as humans, animals and the like, or images inside various machines or facilities, and (ii) displays thus captured images. The imaging system of this kind includes, for example, (a) an imaging module (e.g. an endoscope) which is inserted into a living body and captures an image inside the living body, (b) an image processing device which processes the image captured by the imaging module so that the image can be displayed, and (c) a display device which displays the image that is outputted from the image processing device.

In conventional imaging modules, there have been two types, one of which is a repeated use type imaging module that can be repeatedly used many times (e.g. several thousand times) and the other one of which is a disposable type imaging module that is to be disposed after one-time use as disclosed in, for example, Patent Literature 1.

CITATION LIST

Patent Literatures

Patent Literature 1

US Patent Application Publication No. 2011-0218457 (Publication Date: Sep. 8, 2011)

SUMMARY OF INVENTION

Technical Problem

A repeated use type imaging module requires a sterilization treatment such as a washing treatment with a chemical, every time the repeated use type imaging module is used. Accordingly, the repeated use type imaging module requires (i) use of a material and (ii) a structure which material and structure are resistant to the sterilization treatment that is performed many times (for example, several thousand times). This results in high introduction cost of the repeated use type imaging module. On the other hand, a disposable type imaging module requires no sterilization processing and therefore, allows use of a low-cost material and a low cost structure. Therefore, introduction cost for the disposable type imaging module is low. However, running cost for the disposable type imaging module is high because the disposable type imaging module is disposed after one-time use. In this way, the repeated use type imaging module has a problem that introduction cost is high while the disposable type imaging module has a problem that running cost is high.

In order to solve the above problems, it is possible to consider a low-repeated-use type imaging module that can be repeatedly used a small number of times (for example, approximately 10 to 20 times). The low-repeated use type imaging module only requires (i) use of a material and (ii) a structure which material and structure are resistant to a sterilization treatment that is performed a certain number of times (e.g., 10 to 20 times). This makes it possible to reduce introduction cost. In addition, running cost can be reduced because the low-repeated-use type imaging module can be used a plurality of number of times.

However, for such a low-repeated-use type imaging module, there has been no proposal as to a suitable configuration in which, even in a case where the imaging module is used in a state where the imaging module is connected to a different image processing device, how many times the imaging module has been used can be easily checked on the image processing device. Therefore, there is a demand for development of such a configuration.

The present invention is attained in view of the above problem. An object of the present invention is to provide an imaging module having a suitable configuration that makes it possible to check, on an image processing device to which the imaging module is connected, how many times the imaging module has been used, which imaging module can be used a two or more limited number of times, and to provide an imaging system including the imaging module.

Solution to Problem

In order to solve the above problems, an imaging module in accordance with one aspect of the present invention is an imaging module capable of being used a two or more limited number of times, the imaging module including: an imaging sensor; and a storage device in which the number of use times is stored, the number of use times being the number of times the imaging module is used.

Advantageous Effects of Invention

The configuration of the present invention makes it possible to reduce introduction cost and running cost of the imaging module. Further, the configuration also makes it possible to easily check, on an image processing device to which the imaging module is connected, how many times the imaging module has been used.

BRIEF DESCRIPTION OF DRAWINGS

FIG. 4 is a flow chart illustrating an operation of the imaging system as illustrated in FIG. 1.

FIG. 5 is a flow chart illustrating an operation of an imaging system according to another embodiment of the present invention.

DESCRIPTION OF EMBODIMENTS

Embodiment 1

The following discusses an embodiment of the present invention, with reference to drawings.

(Configuration of Imaging System 1)

Figure 1:
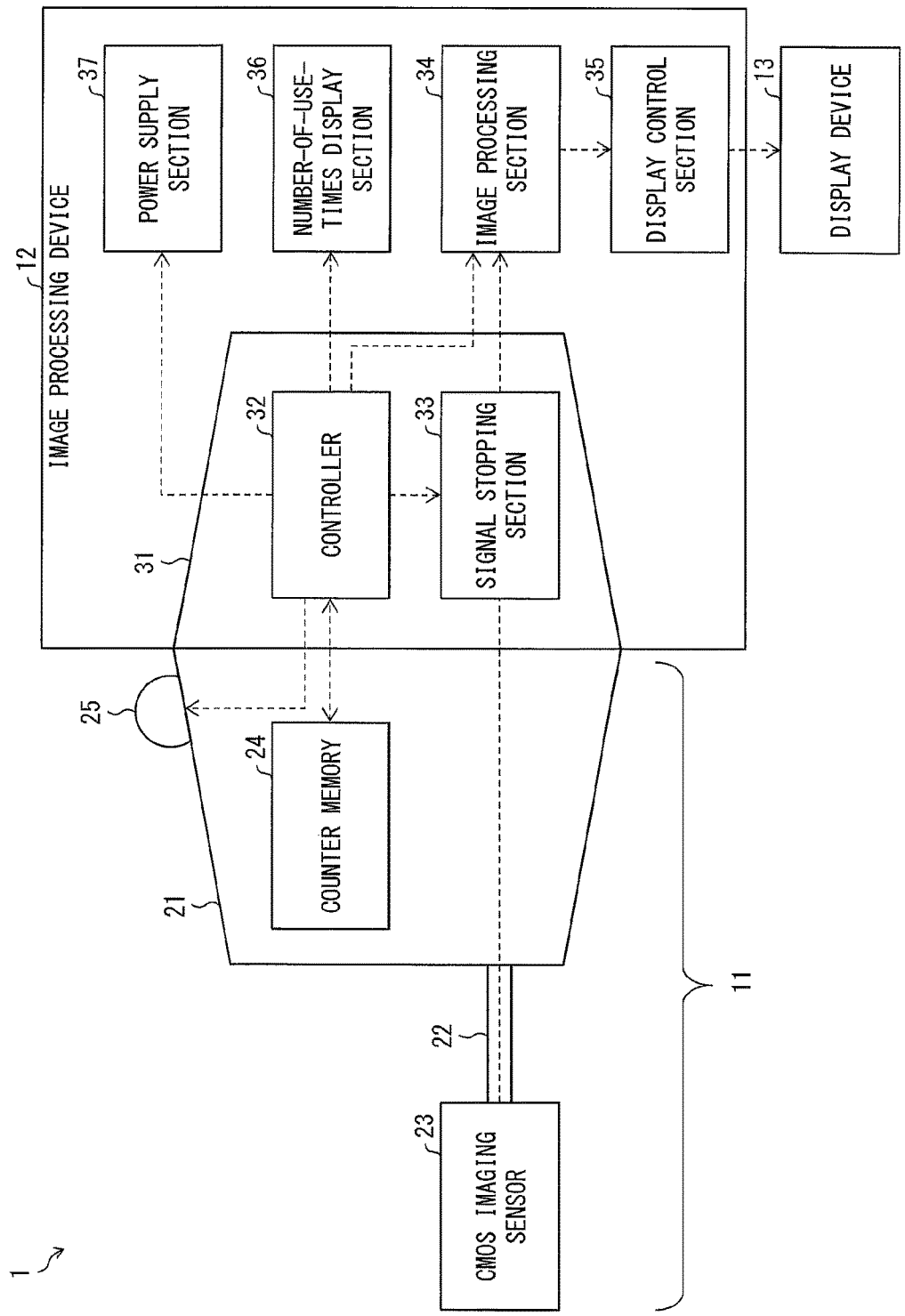
FIG. 1 is a block diagram illustrating a configuration of an imaging system according to an embodiment of the present invention.

FIG. 1 is a block diagram illustrating a configuration of an imaging system 1 of Embodiment 1. As illustrated in FIG. 1, the imaging system 1 of Embodiment 1 includes an imaging module 11, an image processing device 12, and a display device 13.

The imaging module 11 includes a plug (second connector) 21, an image transmission cable 22, a CMOS imaging sensor 23 (solid imaging element), a counter memory (storage device) 24, and an alarm lamp (warning display section) 25. The image processing device 12 includes a receptacle (first connector) 31, a controller (control section) 32, a signal stopping section 33, an image processing section 34, a display control section 35, a number-of-use-times display section 36, and a power supply section 37.

(Configuration of Imaging Module 11)

The imaging module 11 is a low-repeated-use type imaging module that can be used a plurality of number of times with an upper limit of, for example, 20 times. This imaging module 11 can be used a plurality of times, by performing a sterilization treatment after each use. The sterilization treatment is performed by (i) first detaching the imaging module 11 from the image processing device 12 and (ii) then washing the imaging module 11 with, for example, a liquid chemical. Therefore, the imaging module 11 is made from a material that is resistant to the sterilization treatment that is performed the upper limit number of times, and also has a structure (e.g., waterproof function) that is resistant to the sterilization treatment that is performed the upper limit number of times.

In the imaging module 11, the plug 21 is detachably attached to the receptacle 31 of the image processing device 12. This allows the imaging module 11 to be detachably attached to the image processing device 12.

The CMOS imaging sensor 23 is provided to an end part of the image transmission cable 22, and outputs an image signal or a video signal (hereinafter, simply referred to "image signal") that is obtained in an imaging operation. Note that the imaging module 11 can include another type of imaging sensor instead of the CMOS imaging sensor 23.

The image transmission cable 22 is, for example, approximately 2 meters long. An end of the image transmission cable 22 is connected to the plug (second connector) 21, so that an image (image signal) obtained by the CMOS imaging sensor 23 is transmitted to the plug 21.

The counter memory 24 is, for example, a two-or-more-bit nonvolatile memory. The counter memory 24 is provided inside the plug 21, and stores the number of use times of the imaging module 11.

When the number of use times of the imaging module 11 becomes greater than an upper limit value, the alarm lamp 25 is caused to light up so as to inform a user that the number of use times of the imaging module 11 has become greater than the upper limit value. Accordingly, the alarm lamp 25 is provided to the plug 21 so that a user can see whether or not the alarm lamp 25 is lit up.

(Configuration of Image Processing Device 12)

In the image processing device 12, the controller 32 and the signal stopping section 33 is provided inside the receptacle 31. To the receptacle 31, the plug 21 of the imaging module 11 is detachably attached.

In a case where the plug 21 is attached to the receptacle 31, the alarm lamp 25 and the counter memory of the imaging module 11 are connected to the controller 32. Meanwhile, a signal path for signals having been transmitted from the CMOS imaging sensor 23 to the plug 21 through the image transmission cable 22 is connected to the signal stopping section 33.

The power supply section 37 supplies power to the controller 32, the signal stopping section 33, the image processing section 34, the display control section 35, the number-of-use-times display section 36, and other sections of the image processing device 12. In a state where the plug 21 is attached to the receptacle 31, the power supply 37 also supplies power to the CMOS imaging sensor 23, the counter memory 24, and the alarm lamp 25 of the imaging module 11.

The signal stopping section 33 is connected to the image processing section 34, and performs a signal stopping operation under control of the controller 32. This signal stopping operation stops signals which are to be transmitted from the CMOS imaging sensor 23 of the imaging module 11 to the signal processing section 34 of the image processing device 12 and required for display of an image on the display device 13. The signal stopping section 33 can be a switching means which is made of a relay or a semiconductor switching device and simply blocks the signal path from the CMOS imaging sensor 23 to the image processing section 34.

The above signals required for display of an image on the display device 13 encompasses a synchronization signal in addition to the image signal. Therefore, the signal stopping section 33 can be configured to stop transmission of at least either one of the image signal and the synchronization signal.

Figure 2:
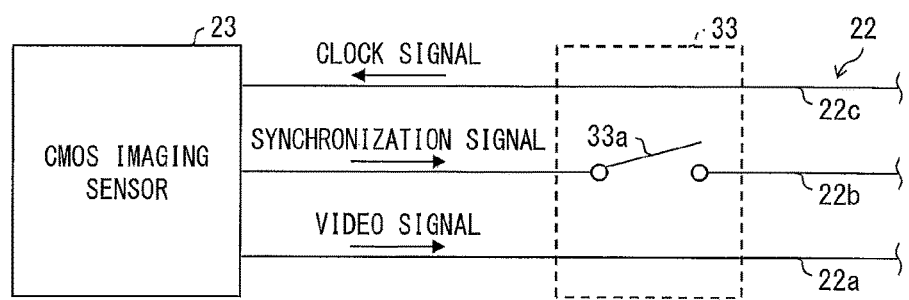
FIG. 2 is a circuit diagram schematically illustrating an example of a signal stopping section that stops a synchronization signal contained in output signals from a CMOS imaging sensor as illustrated in FIG. 1.

In a case where the signal stopping section 33 stops the synchronization signal, an image displayed on the display device 13 forms a monochrome screen such as a solid blue screen. This is because the image signal cannot be synchronized. In this case, it is easy for a user to recognize that the number of use times of the imaging module 11 becomes greater than the upper limit value, in other words, that the imaging module 11 is no longer usable. FIG. 2 is a circuit diagram schematically illustrating an example of the signal stopping section 33 including a switch 33a that stops the synchronization signal described above.

The image processing section 34 processes the image signals transmitted from the CMOS imaging sensor 23, so as to generate image signals that the display device 13 can display. The display control section 35 controls the display device 13 so that the display device 13 displays the image signals generated by the image processing section 34.

The number-of-use-times display section 36 is a display section made of, for example, an LED lamp. The number-of-use-times display section 36 displays, under control of the controller 32, the number of use times of the imaging module 11 connected to the image processing device 12.

The controller 32 counts the number of use times of the imaging module 11, and causes the counter memory 24 to store a count value, that is, the number of use times of the imaging module 11.

The following is an example of a method of counting the number of use times by use of the image processing device 12. The controller 32 determines that the imaging module is used one time, in a case where the controller 32 detects that the power supply section 37 supplies power to the imaging module 11 continuously for a predetermined period of time (e.g. approximately 10 minutes) after the image processing device 12 is powered on. Next, the controller 32 updates a count value that is stored in the counter memory 24. Further, the controller 32 causes the number-of-use-times display section 36 to display thus updated count value.

The controller 32 monitors whether or not the count value that is stored in the counter memory 24 becomes greater than the upper limit value (threshold value) of the number of use times of the imaging modules 11. Further, in a case where the count value becomes greater than the upper limit value (the threshold value), the controller 32 controls the signal stopping section 33 so that transmission of image signals to the image processing section 34 stops. In this case, the controller 32 performs a notification processing for informing a user that because the number of use times of the imaging module 11 has become greater than the threshold value, the imaging module 11 is no longer usable.

In the notification processing, the controller 32 causes the alarm lamp 25 to light up, so as to inform the user that because the number of use times of the imaging module 11 has become greater than the threshold value, the imaging module 11 is no longer usable. The controller 32 can alternatively control the image processing section 34 so as to display, on the display device 13, one or both of (a) a message that the number of use times of the imaging module 11 has become greater than the threshold value and (b) a message that the imaging module 11 is no longer usable. As a further alternative, the controller 32 can inform by sound that because the number of use times of the imaging module 11 has become greater than the threshold value, the imaging module 11 is no longer usable.

Note that the above message(s) to be displayed by the display device 13 and a message(s) below can be stored in the controller 32. Further, in a case where any of the messages is displayed on the display device 13 in a manner such that the message is superimposed on a display image, the image processing section 34 can perform a processing for superimposing the message(s) on the display image.

Note also that the controller 32 can be configured such that, in a case where the controller 32 determines that the number of use times of the imaging module 11 becomes greater than the upper limit value after the image processing device 12 is powered on, use of the imaging module 11 at this time is still allowed, that is, the controller 32 does not cause the signal stopping section 33 to perform the signal stopping operation at this time. In this case, the controller 32 causes the signal stopping section 33 to perform the signal stopping operation when the image processing device 12 is powered on next time.

Alternatively, the controller 32 can be configured such that in a case where the controller 32 determines that the number of use times of the imaging module 11 reaches the upper limit value after the image processing device 12 is powered on, the controller 32 causes the display device 13 to display a message that the number of use times of the imaging module 11 has reached the upper limit value and a message that the imaging module 11 used this time will be unusable from next time.

(Example of Imaging Module 11)

Figure 3:
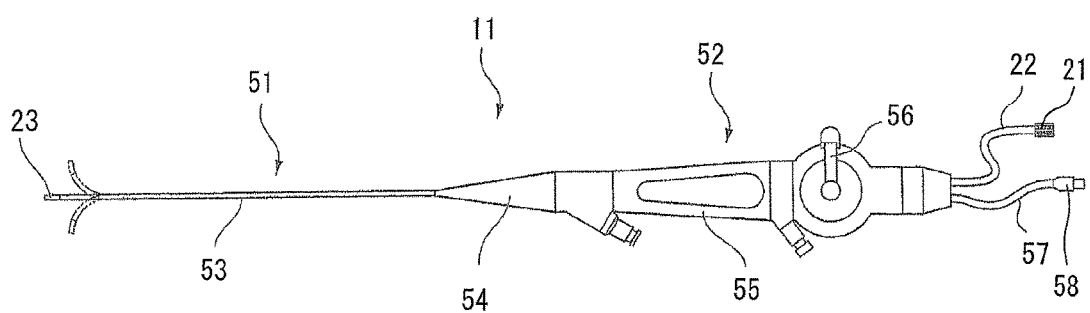
FIG. 3 is an elevation view illustrating an example of an appearance of the imaging module as illustrated in FIG. 1.

FIG. 3 is an elevation view illustrating an example of an appearance of the imaging module 11. The imaging module 11 illustrated in FIG. 3 includes an insertion section 51 and an operating section 52. The insertion section 51 is a long portion that is to be inserted into an observation region of a subject. The operating section 52 is a portion for holding and operating the imaging module 11. This operating section 52 is provided to an end opposite to the insertion section 51.

The insertion section 51 includes a main body portion 53 for insertion and a bending stopper portion 54. The main body portion 53 for insertion includes the CMOS imaging sensor 23 at an end part of the main body portion 53 for insertion.

The operating section 52 includes a main body portion 55 for operation, an operation lever 56, a light guide cable 57, a plug 58, the image transmission cable 22, and the plug 21. The operation lever 56 is used for a bending operation of the vicinity of an end part of the insertion section 51. In other words, in the imaging module illustrated in FIG. 3, the bending operation of the vicinity of the insertion section 51 can be performed, by operating the operation lever 56 and thereby driving an angle wire (not illustrated).

The image transmission cable 22 is provided with the plug 21. This plug 21 is connected to the receptacle 31 of the image processing device 12. The light guide cable 57 is connected to a light guide (not illustrated) which is provided inside the insertion section 51, and the plug 58 is provided to an end of the light guide cable 57. Accordingly, light is introduced into the imaging module 11 by connecting the plug 58 to an external light guide (not illustrated).

The following discusses an operation of the imaging system 1 in the above configuration. FIG. 4 is a flowchart illustrating an operation of the imaging system 1.

When the image processing device 12 is powered on (S11), the controller 32 determines whether or not the plug 21 of the imaging module 11 is connected to the receptacle 31 of the image processing device 12, in other words, whether or not power is supplied to the imaging module 11 from the power supply section 37 (S12). This determination can be made based on, for example, whether or not the controller 32 can communicate with the counter memory 24.

Next, if a result of the determination at S12 is "YES", the controller 32 determines whether or not a count value of the number of use times of the imaging module 11 connected was greater than the upper limit value (threshold) in previous use of the imaging module 11 (S13). This determination can be performed based on contents stored in the counter memory 24.

Next, if a result of the determination at S13 is "YES", the controller 32 performs a notification processing so as to inform a user that the imaging module 11 connected is unusable. In this notification processing, the controller 32 causes (1) the alarm lamp 25 to light up, (2) the display device 13 to display a message that the imaging module 11 connected is unusable, and (3) the signal stopping section to perform the signal stopping operation described earlier.

Note that the controller 32 should cause at least one of the above (1) through (3) as the notification processing. However, it is preferable to perform the processing of causing the above (3) so as to reliably make the imaging module 11 unusable. In addition to the processing of causing the above (3), it is preferable to perform the processing of causing the above (1) or (2) or the processing of causing the above (1) and (2).

On the other hand, if the result of the determination at S13 is "NO", the controller 32 determines whether or not the imaging module 11 is kept connected continuously for a predetermined period of time after the imaging module 11 is powered on, in other words, whether or not a predetermined time has elapsed after the start of power supply to the imaging module 11 from the power supply section 37 (S14).

If a result of the determination at S14 is "YES", the controller 32 updates the count value (i.e., the number of use times of the imaging module 11 connected) stored in the counter memory 24, that is, increments the count value by +1 (S15). Thereafter, the controller 32 causes the numberof-use-times display section 36 to display the updated number of use times of the imaging module 11 (S16).

Next, the controller 32 determines whether or not the count value stored in the counter memory 24 is greater than the upper limit value of the number of use times of the imaging module 11 (S17). If a result of this determination is "NO", the controller 32 directly ends processing.

On the other hand, if the result of the determination at S17 is "YES", the controller 32 causes the counter memory 24 to record that the count value is greater than the upper limit value, and then ends the processing (S18).

Note that, in the above operation, the image processing section 34 may stop, under control of the controller 32, image processing for causing the display device 13 to display an image obtained by the CMOS imaging sensor 23, in place of the signal stopping operation performed by the signal stopping section 33.

(Advantages of Imaging Module 11 and Imaging System 1)

As described above, in the imaging system 1 of Embodiment 1, the imaging module 11 is a low-repeated-use type imaging module that can be used a plurality of number of times with an upper limit of, for example, 20 times. This makes it possible to reduce introduction cost and running cost.

In a case where the number of use times of the imaging module 11 becomes greater than the upper limit value, a notification processing is performed. In the notification processing, at least one of the following (1) to (3) is performed: (1) to cause the alarm lamp 25 to light up, (2) to cause the display device 13 to display a message that the imaging module 11 is unusable, and (3) to cause the signal stopping section 33 to perform an operation of stopping an image signal and the like that is to be transmitted to the image processing section 34. This allows a user to easily recognize that the imaging module 11 connected to the image processing device 12 is no longer usable because the number of use times of the imaging module 11 has become greater than an upper limit number of use times.

In a case where the signal stopping section 33 is caused to perform the operation of stopping an image signal and the like that is to be transmitted to the image processing section 34, the imaging module 11 which has been used more than an upper limit number of times can be reliably made unusable. Therefore, it is possible to reliably prevent use of the imaging module 11 which has been used more than the upper limit number of times.

Further, the number-of-use-times display section 36 displays the current number of use times of the imaging module 11 at the point of the present use of the imaging module 11. This allows a user to easily know the current number of use times of the imaging module 11 at the present use, by checking a display of the number-of-use-times display section 36.

Further, the current number of use times of the imaging module 11 is stored in the counter memory 24. Accordingly, even in a case where the imaging module 11 having been previously connected to a first image processing device is connected to a second imaging processing device 12 this time and used, a controller 32 of the second image processing device 12 can easily obtain the current number of use times of the imaging module 11, by checking contents stored in the counter memory 24.

Embodiment 2

The following discusses another embodiment of the present invention, with reference to drawings. FIG. 5 is a flowchart illustrating an operation of an imaging system 1 of Embodiment 2.

Note that steps in FIG. 5 that are identical to those of steps in FIG. 4 are given identical step (S) numbers, respectively. These steps in FIG. 5 have already been described with reference to FIG. 4, and therefore, description of the above steps in FIG. 5 is omitted here.

According to Embodiment 1, the controller 32 is configured not to perform a notification processing at the time when the number of use times of the imaging module 11 connected to the image processing device 12 becomes greater than an upper limit value, but to perform a notification processing at the time when the imaging module 11 is used next time that follows the time when the number of use times of the imaging module 11 has become greater than the upper limit value. However, according to Embodiment 2, as illustrated in FIG. 5, a controller 32 is configured to perform a notification processing (S19) at the time when the number of use times of an imaging module 11 connected to an image processing device 12 becomes greater than an upper limit value (S17).

The imaging module 11 of Embodiment 2 is configured to be the same as the imaging module 11 of Embodiment 1, except only the above-described point. Accordingly, advantageous effects and the like of the imaging module 11 and an imaging system 1 of Embodiment 2 are the same as those of Embodiment 1.

Note that, in Embodiments 1 and 2, the alarm lamp 25 can be provided not to the plug 21 of the imaging module 11 but to the image processing device 12.

Further, the plug 21 as a connector is attached to/detached from the image processing device 12, that is, the receptacle 31 a smaller number of times, because the imaging module 11 is a low-repeated-use type imaging module. Therefore, the plug 21 can be an inexpensive card-edge type plug.

CONCLUSION

An imaging module in accordance with a first aspect of the present invention, is an imaging module capable of being used a two or more limited number of times, the imaging module including: an imaging sensor; and a storage device in which the number of use times is stored, the number of use times being the number of times the imaging module is used.

The above configuration described above allows the imaging module to be used a two or more limited number of times. Accordingly, as compared to an imaging module of a type that can be repeatedly used many times, the imaging module of the present invention can have, for example, lower durability to washing treatments with chemicals, and therefore, introduction cost can be reduced. Further, as compared to a disposable imaging module that is to be disposed after one-time use, running cost of the imaging module of the present invention can be reduced.

Moreover, the imaging module includes a storage device in which the number of use times (the number of times that the imaging module is used) is stored. This number of use times is counted by, for example, a control section. This makes it possible to easily check the number of use times of the imaging module on an image processing device to which the imaging module is connected.

An imaging system in accordance with a second aspect of the present invention is configured to include the imaging module in accordance with the first aspect of the present invention, and a control section that counts the number of use times and stores, in the storage device, the number of use times counted.

The above configuration makes it possible to update, by the control section, the number of use times stored in the storage device, every time the imaging module is used. Further, in a case where the number of use times becomes greater than a threshold value, a notification processing can be performed as appropriate by the control section so as to inform a user that the imaging module is unusable.

An imaging system in accordance with a third aspect of the present invention can be configured to further include a warning display section, the control section causing the warning display section to light up in a case where the number of use times becomes greater than a threshold value, in the imaging system in accordance with the second aspect.

In the above configuration, in a case where the number of use times of the imaging module becomes greater than the threshold value, the warning display section is caused to light up. This allows a user to easily recognize that the number of use times of the imaging module is greater than the threshold value and therefore, the imaging module is unusable.

An imaging system in accordance with a fourth aspect of the present invention can be configured to further include: an image stopping section provided in a signal path through which signals outputted from the imaging sensor are transmitted, the image stopping section stopping transmission of the signals in the signal path, the control section controlling the signal stopping section so that, in a case where the number of use times becomes greater than the threshold value, transmission of the signals through the signal path is stopped, in the imaging module in accordance with the above aspect 2 or 3.

In the above configuration, in a case where the number of use times of the imaging module becomes greater than the threshold value, the signal stopping section stops the signals that are outputted from the imaging sensor. Consequently, the display device for displaying the signals outputted from the imaging sensor stops display of an image signal or a video signal contained in the signals. This allows a user to easily recognize that the number of use times of the imaging module is greater than the threshold value and therefore, the imaging module is unusable.

Further, the configuration makes it possible to reliably prevent a situation in which an unusable imaging module is used, because the display device stops display of an image signal or a video signal that is outputted from the imaging sensor.

An imaging system in accordance with a fifth aspect of the present invention can be configured such that in the imaging system in accordance with the fourth aspect, the signals outputted from the imaging sensor includes (i) a video signal or an image signal and (ii) a synchronization signal; and the signal stopping section is provided in the signal path of the synchronization signal.

In the above configuration, in a case where the number of use times of the imaging module becomes greater than the threshold value, the signal stopping section stops transmission of the synchronization signal among the signals outputted from the imaging sensor. Accordingly, in the display device which displays the signals outputted from the imaging sensor, the video signal or the image signal cannot be synchronized. This results in, for example, a solid blue screen.

In a case where the video signal or the image signal is stopped, a screen of the display device turns dark. Such a dark screen is a little confusing as to whether the display device is (i) in a state displaying a signal of an image captured by the imaging sensor in a dark part inside a subject or in a state in which a signal outputted from the imaging sensor is stopped. On the other hand, in a case where the synchronization signal is stopped, the display screen becomes, for example, a solid blue screen as described above. Therefore, it is easy to recognize that the display device is in a state in which the signal is stopped.

An imaging system in accordance with a sixth aspect of the present invention can be configured to further include: a number-of-use-times display section, the control section causing the number-of-use-times display section to display the number of use times, in the imaging system in accordance with any one of the second aspect through the fifth aspect.

In the above configuration, the number-of-use-times display section displays the current number of use times of the imaging module at the point of the present use of the imaging module. This allows a user to easily know the current number of use times of the imaging module at the present use of the imaging module, by checking a display of the number-of-use-times display section.

An imaging system in accordance with the seventh aspect of the present invention can be configured to further include: a display device; and an image processing device including an image processing section that processes the signals outputted from the imaging sensor, so as to convert the signals outputted from the image sensor into signals in a form that allows the display device to display the signals, the control section controlling the image processing section so that, in a case where the number of use times becomes greater than the threshold value, the display device displays (a) a message that the number of use times has become greater than the threshold value or (b) a message that the imaging module is unusable, in the imaging system in accordance with any one of the second aspect through the sixth aspect.

In the above configuration, in a case where the number of use times of the imaging module becomes greater than the threshold value, the display device displays (a) the message that the number of use times has become greater than the threshold value or (b) the message that the imaging module is unusable. This allows a user to easily recognize that (a) the number of use times of the imaging module has become greater than the threshold value or (b) the imaging module is unusable, from the message that is displayed on the display device.

An imaging system in accordance with an eighth aspect of the present invention can be configured to include: a first connector in which the control section is provided, the imaging module including a second connector in which the storage device is provided, the second connector being detachably attached to the first connector, in the imaging system in accordance with any one of the second aspect through the seventh aspect of the present invention.

The above configuration makes it possible to provide a compact imaging system which includes: the imaging module including the second connector in which the storage device is provided; and the first connector in which the control section is provided, the first connector being detachably attached to the second connector of the imaging module.

The present invention is not limited to the description of the embodiments above, but may be altered by a skilled person within the scope of the claims. An embodiment based on a proper combination of technical means disclosed in different embodiments is encompassed in the technical scope of the present invention.

INDUSTRIAL APPLICABILITY

The present invention can be applied to an endoscope system used in a medical field or in a field of inspecting various machines and facilities.

REFERENCE SIGNS LIST

1 Imaging system
11 Imaging module
12 Image processing device
13 Display device
21 Plug (second connector)
22 Image transmission cable
23 CMOS imaging sensor
24 Counter memory (storage device)
25 Alarm lamp (warning display section)
31 Receptacle (first connector)
32 Controller (control section)
33 Signal stopping section
34 Image processing section
35 Display control section
36 Number-of-use-times display section

The invention claimed is:

1. An imaging system comprising:
an imaging module capable of being used a two or more limited number of times, the imaging module comprising:
an imaging sensor that outputs (i) a video signal or an image signal and (ii) a synchronization signal for use in displaying, on a display device, a video represented by the video signal or an image represented by the image signal, and
a storage device in which the number of use times is stored, the number of use times being the number of times the imaging module is used;
a control section that counts the number of use times and stores, in the storage device, the number of use times counted; and
a signal stopping section provided in a signal path through which the synchronization signal outputted from the imaging sensor is transmitted, the signal stopping section stopping transmission of the synchronization signal in the signal path,
the control section controlling the signal stopping section so that, in a case where the number of use times becomes greater than the threshold value, transmission of the synchronization signal through the signal path is stopped.

2. The imaging system as set forth in claim 1, further comprising:

a warning display section,
the control section causing the warning display section to light up in a case where the number of use times becomes greater than a threshold value.

3. The imaging system as set forth in claim 1, further comprising:
a number-of-use-times display section,
the control section causing the number-of-use-times display section to display the number of use times.

4. The imaging system as set forth in claim 1, further comprising:
a display device; and
an image processing device including an image processing section that processes the signals outputted from the imaging sensor, so as to convert the signals outputted from the image sensor into signals in a form that allows the display device to display the signals,
the control section controlling the image processing section so that, in a case where the number of use times becomes greater than the threshold value, the display device displays (a) a message that the number of use times becomes greater than the threshold value or (b) a message that the imaging module is unusable.

5. The imaging system as set forth in claim 1, further comprising:
a first connector in which the control section is provided,
the imaging module including a second connector in which the storage device is provided, the second connector being detachably attached to the first connector.

6. The imaging system as set forth in claim 1, wherein the signal stopping section stops supply of the signals to an image processor.

7. The imaging system as set forth in claim 1, wherein:
the signal stopping section stops the transmission of the synchronization signal through the signal path without stopping transmission of the video signal or the image signal; and
the control section controls the signal stopping section so that, in the case where the number of use times becomes greater than the threshold value, the transmission of the synchronization signal through the signal path is stopped but transmission of the video signal or the image signal is not stopped.

8. The imaging system as set forth in claim 1, further comprising the display device,
the display device displaying a solid blue screen in a case where the transmission of the synchronization signal through the signal path is stopped.

* * * * *